(12) United States Patent
Sasaki et al.

(10) Patent No.: US 10,234,472 B2
(45) Date of Patent: Mar. 19, 2019

(54) AUTOMATIC ANALYSIS DEVICE

(71) Applicant: HITACHI HIGH-TECHNOLOGIES CORPORATION, Tokyo (JP)

(72) Inventors: Hirofumi Sasaki, Tokyo (JP);
Toshihide Hanawa, Tokyo (JP);
Tsuguhiko Satou, Tokyo (JP);
Yoshihiro Naitou, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 120 days.

(21) Appl. No.: 15/313,981

(22) PCT Filed: Apr. 7, 2015

(86) PCT No.: PCT/JP2015/060897
§ 371 (c)(1),
(2) Date: Nov. 25, 2016

(87) PCT Pub. No.: WO2015/182256
PCT Pub. Date: Dec. 3, 2015

(65) Prior Publication Data
US 2017/0212137 A1    Jul. 27, 2017

(30) Foreign Application Priority Data

May 30, 2014 (JP) ................. 2014-113028

(51) Int. Cl.
*G01N 33/00* (2006.01)
*G01N 35/02* (2006.01)
(Continued)

(52) U.S. Cl.
CPC ........... *G01N 35/025* (2013.01); *G01N 21/75* (2013.01); *G01N 35/00* (2013.01);
(Continued)

(58) Field of Classification Search
CPC .......................................... G01N 2035/00891
See application file for complete search history.

(56) References Cited

U.S. PATENT DOCUMENTS

| 2005/0013736 A1* | 1/2005 | McKeever | G01N 35/0092 422/63 |
|---|---|---|---|
| 2005/0175506 A1 | 8/2005 | Matsubara et al. | |

(Continued)

FOREIGN PATENT DOCUMENTS

| CN | 101294973 A | 10/2008 |
|---|---|---|
| CN | 103808946 A | 5/2014 |

(Continued)

OTHER PUBLICATIONS

International Search Report of PCT/JP2015/060897 dated Jul. 7, 2015.
(Continued)

*Primary Examiner* — Kathryn Wright
(74) *Attorney, Agent, or Firm* — Mattingly & Malur, PC

(57) ABSTRACT

Disclosed is an automatic analysis device in which a check item at a time of an analysis start can be set in accordance with a skill level of an operator, an analysis can be performed after the check item being displayed and confirmed, and erroneous measurement caused due to a missed check can be prevented. The check item such as checking the remaining quantity of a reagent or the like displayed in a check screen before the analysis start can be set for each type of operator, each day, each time. The set check item is configured to be displayed in a screen before the analysis start, and unless the operator confirms the check item, the analysis start is not allowed in principle. An automatic analysis device which can prevent erroneous measurement caused due to a missed check of the operator before the analysis start is realized.

13 Claims, 17 Drawing Sheets

(51) Int. Cl.
*G01N 35/00* (2006.01)
*G01N 21/75* (2006.01)

(52) U.S. Cl.
CPC . *G01N 35/00584* (2013.01); *G01N 35/00712* (2013.01); *G01N 35/00722* (2013.01); *G01N 35/02* (2013.01); *G01N 2035/0091* (2013.01); *G01N 2035/00534* (2013.01); *G01N 2035/00891* (2013.01)

(56) References Cited

U.S. PATENT DOCUMENTS

| | | |
|---|---|---|
| 2008/0279048 A1 | 11/2008 | Wakamiya et al. |
| 2009/0234905 A1 | 9/2009 | Yamaguchi et al. |
| 2009/0263281 A1 | 10/2009 | Ushiku et al. |
| 2012/0237400 A1 | 9/2012 | Ikeda et al. |
| 2013/0287593 A1 | 10/2013 | Erwin et al. |
| 2014/0129153 A1 | 5/2014 | Uratani |
| 2014/0170023 A1 | 6/2014 | Saito et al. |

FOREIGN PATENT DOCUMENTS

| | | |
|---|---|---|
| EP | 0359049 A2 | 3/1990 |
| JP | 02-080962 A | 3/1990 |
| JP | 06-160397 A | 6/1994 |
| JP | 09-196924 A | 7/1997 |
| JP | 2002-162400 A | 6/2002 |
| JP | 2003-162400 A | 6/2003 |
| JP | 2003-232797 A | 8/2003 |
| JP | 2004-028932 A | 1/2004 |
| JP | 2006-284380 A | 10/2006 |
| JP | 2008-292159 A | 12/2008 |
| JP | 2009-216639 A | 9/2009 |
| JP | 2010-066108 A | 3/2010 |
| JP | 2011-149905 A | 8/2011 |
| JP | 2012-189552 A | 10/2012 |
| JP | 2013-076619 A | 4/2013 |
| JP | 2013-88933 A | 5/2013 |
| WO | 2013/035418 A1 | 3/2013 |

OTHER PUBLICATIONS

Extended European Search Report received in corresponding European Application No. 15799548.1 dated Jan. 22, 2018.
International Preliminary Report on Patentability received in corresponding International Application No. PCT/JP2015/060897 dated Dec. 8, 2016.
Chinese Office Action received in corresponding Chinese Application No. 201580026081.5 dated Jul. 25, 2017.

* cited by examiner

[Fig. 1]
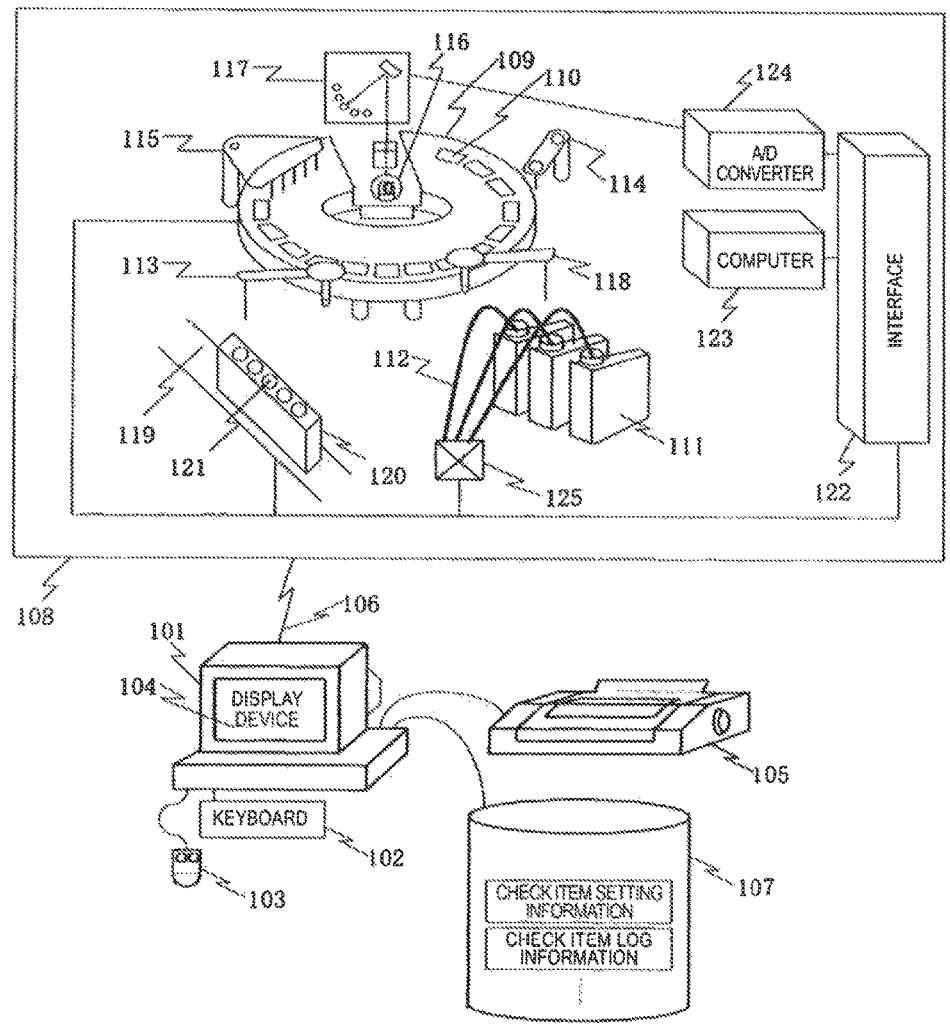

[Fig. 2]
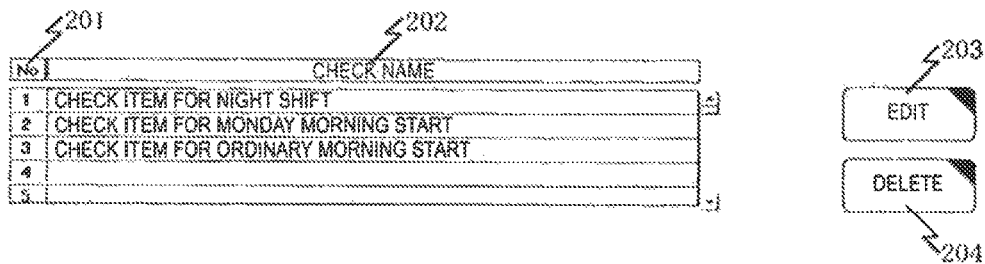

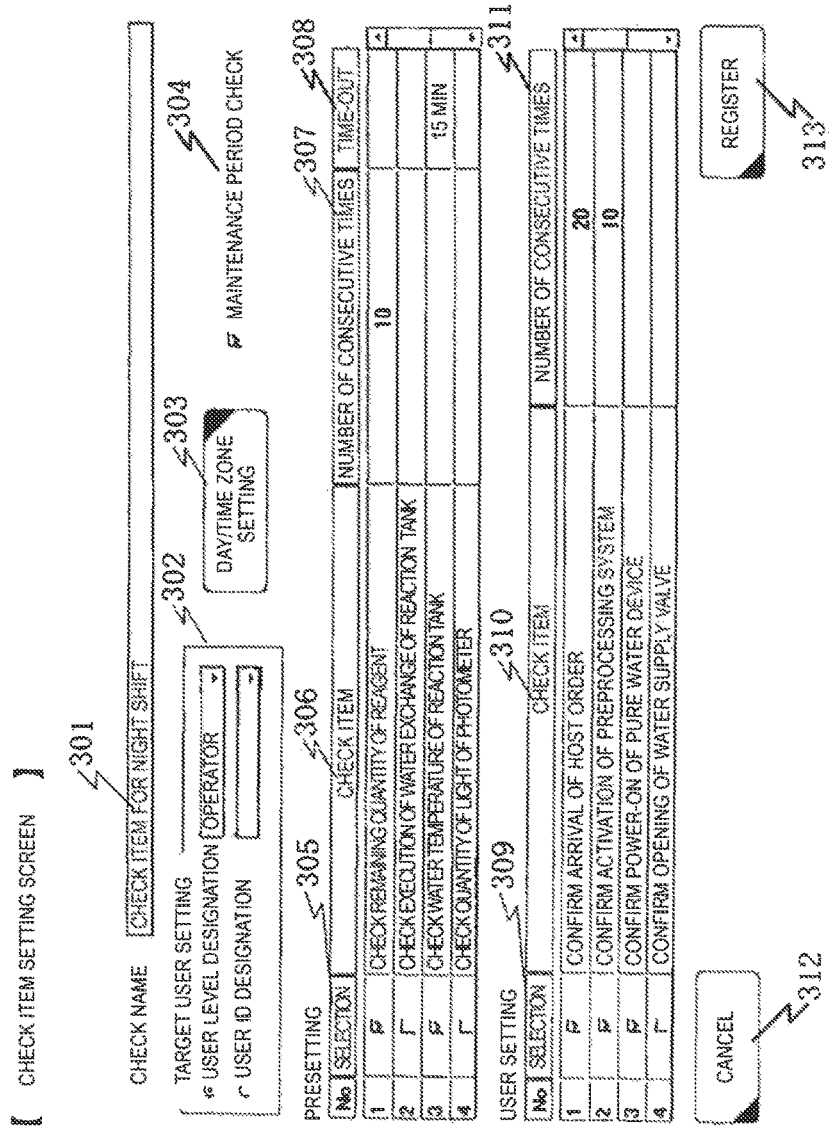
[Fig. 3]

[Fig. 4]
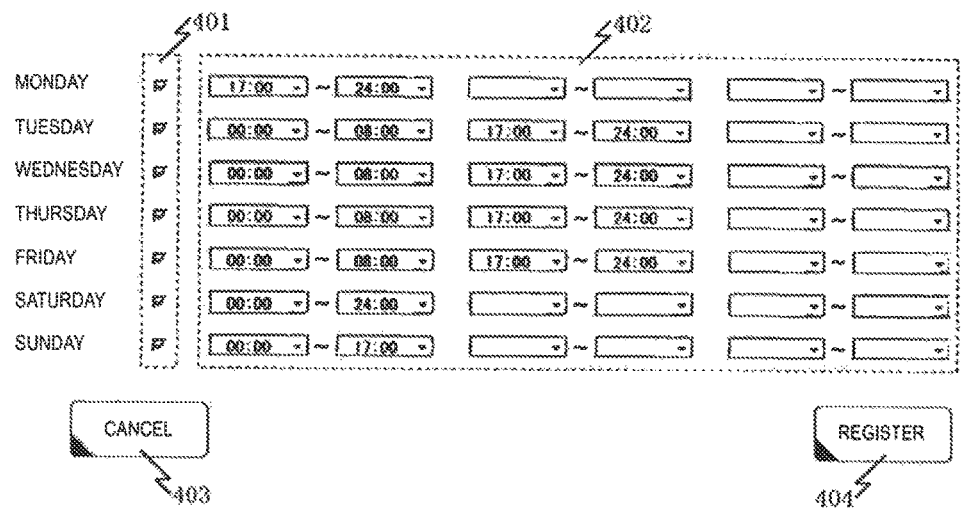

[Fig. 5]
[ MAINTENANCE PERIOD SETTING SCREEN ]
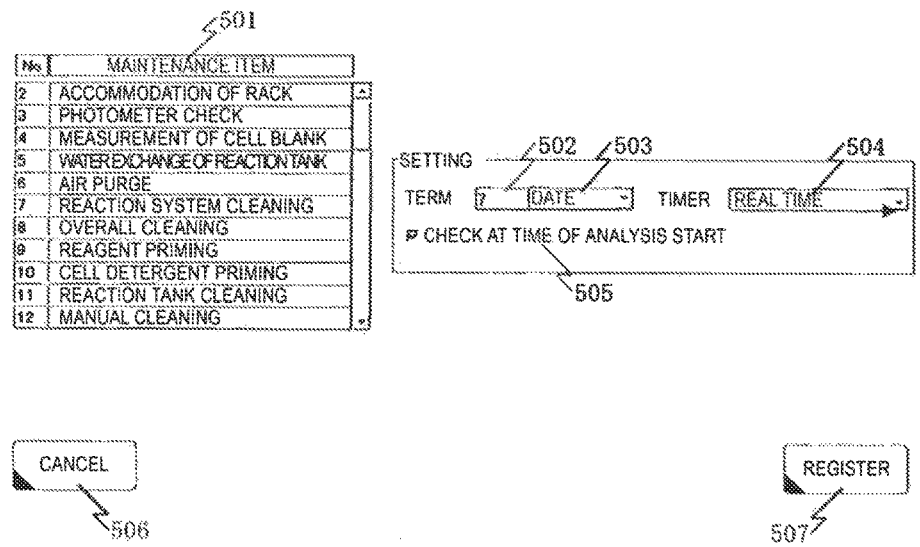
[Fig. 6]
[ MESSAGE LIST SCREEN ]
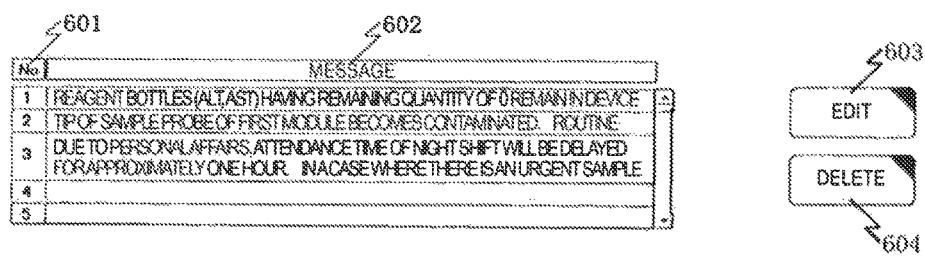

[Fig. 7]
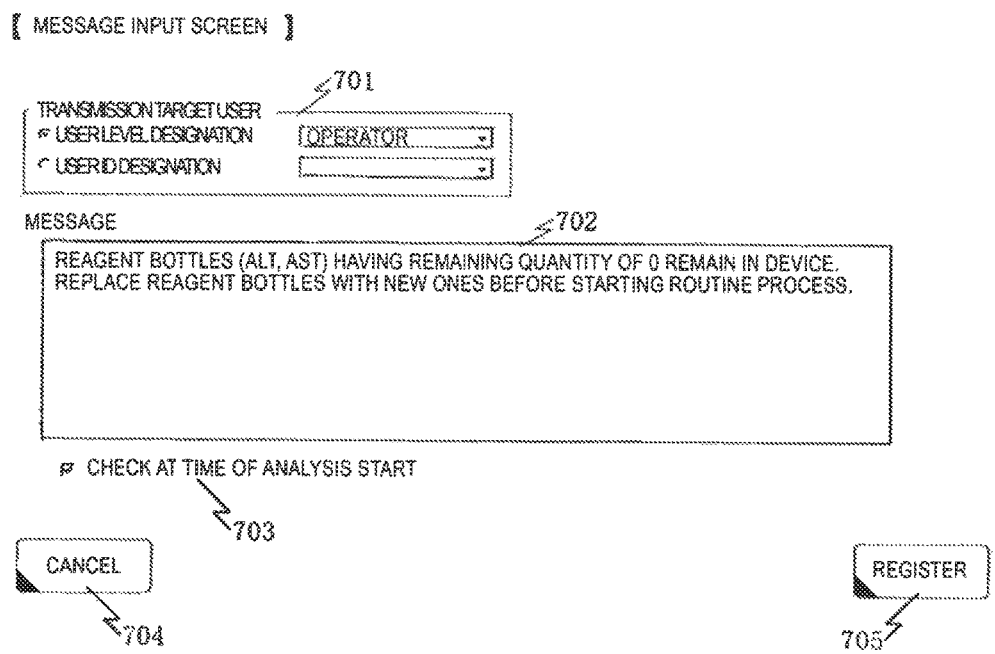

[Fig. 8]
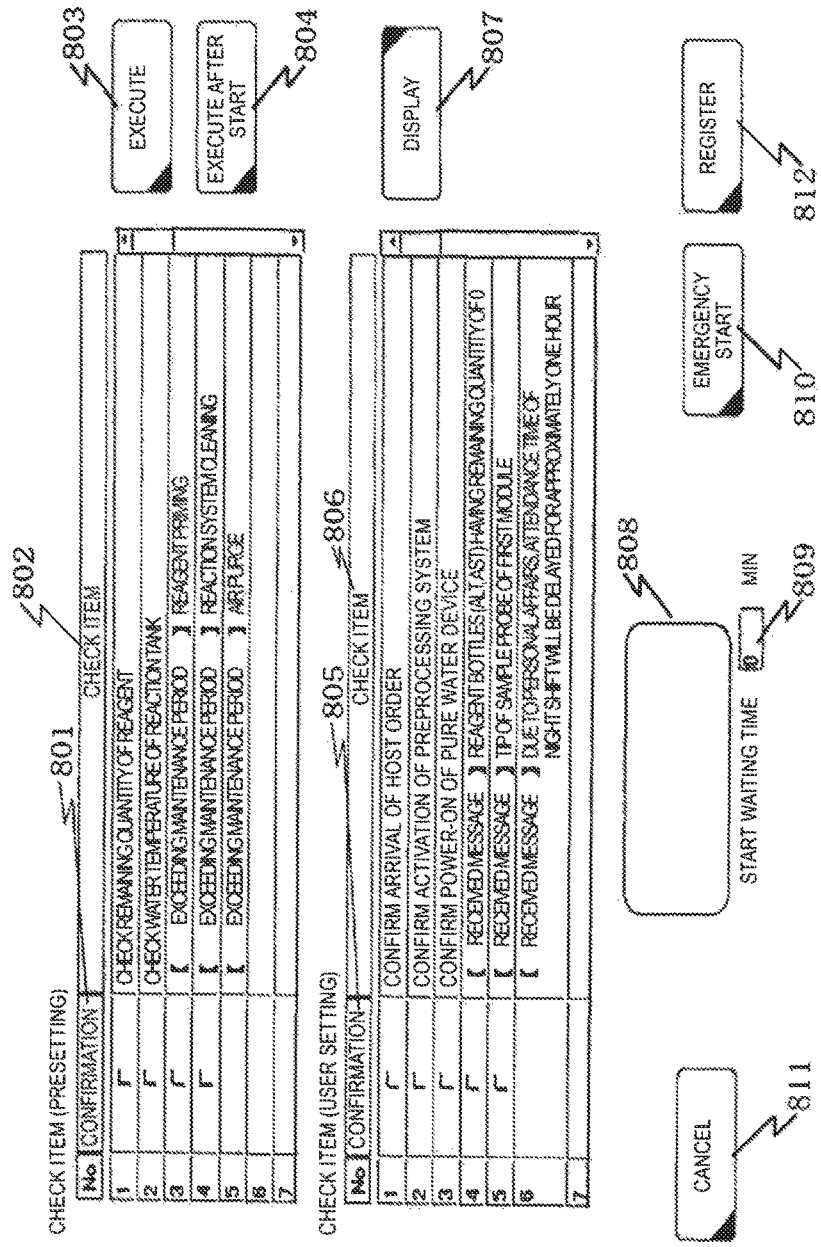

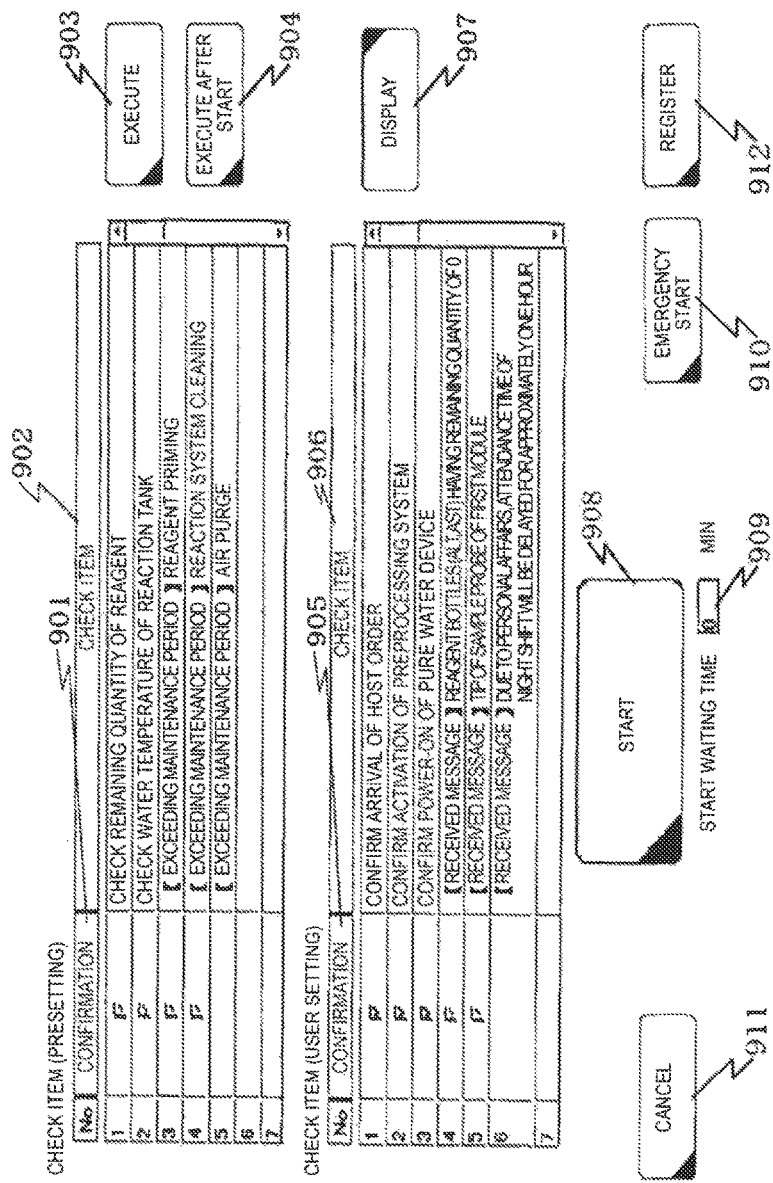
[Fig. 9]

[Fig. 10]
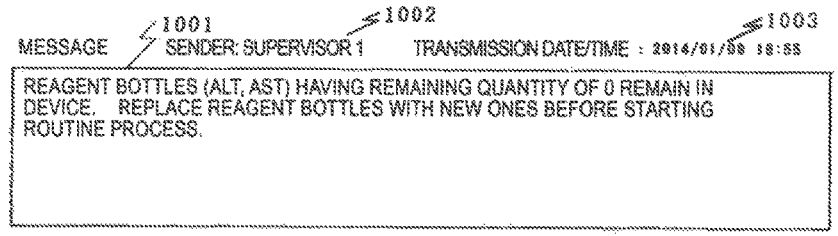

[Fig. 11]

{ ALARM DISPLAY SCREEN }

| NUMBER | ANALYSIS MODULE | LEVEL | ALARM MESSAGE | DATE TIME |
|---|---|---|---|---|
| XXX-XXXXX3 | ANALYSIS MODULE 1 | WARNING | ABNORMAL WATER TEMPERATURE OF REACTION TANK | 13/12/24 18:28 |
| | | | | |
| | | | | |
| | | | | |
| | | | | |
| | | | | |
| | | | | |

DESCRIPTION,
COUNTERMEASURES

NUMBER : XXX-XXXXX3
LEVEL : WARNING
DESCRIPTION : AT TIME OF ANALYSIS START, WATER TEMPERATURE OF REACTION TANK HAS NOT REACHED RANGE (37±0.5°C) TILL TIME-OUT TIME
COUNTERMEASURES : (1) CONFIRM THAT ROOM TEMPERATURE IS WITHIN RANGE FROM 15°C TO 32°C. OPEN FRONT COVER OF DEVICE, AND REMOVE DUST AND THE LIKE IN FILTER OF RADIATOR.
(2) OPEN FRONT COVER OF DEVICE, AND REMOVE DUST AND THE LIKE IN FILTER OF RADIATOR.

[DELETE]  [CLOSE]

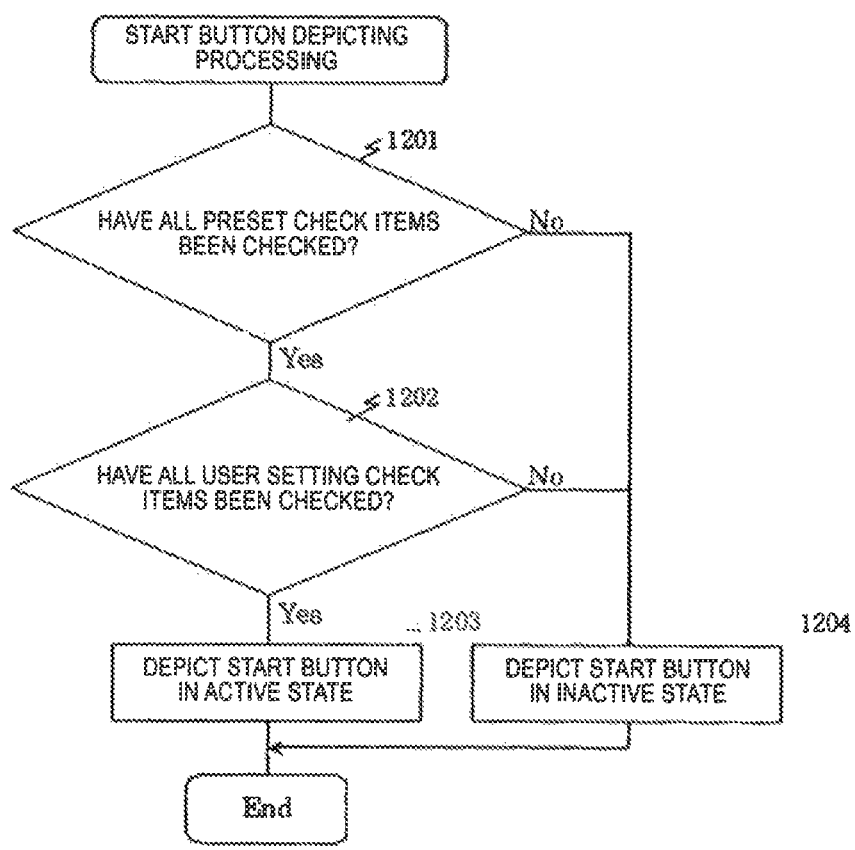

[Fig. 13]
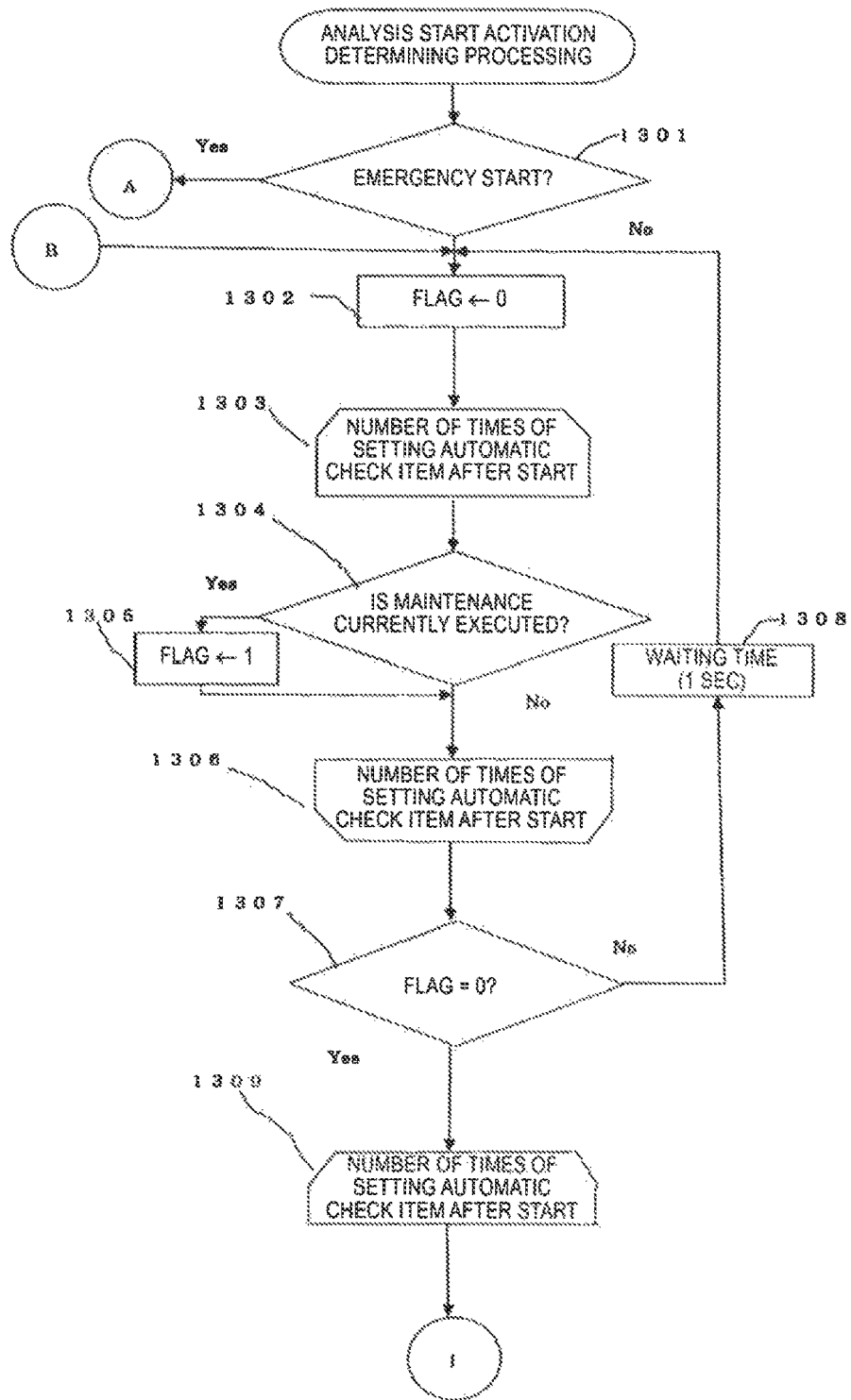

[Fig. 14]
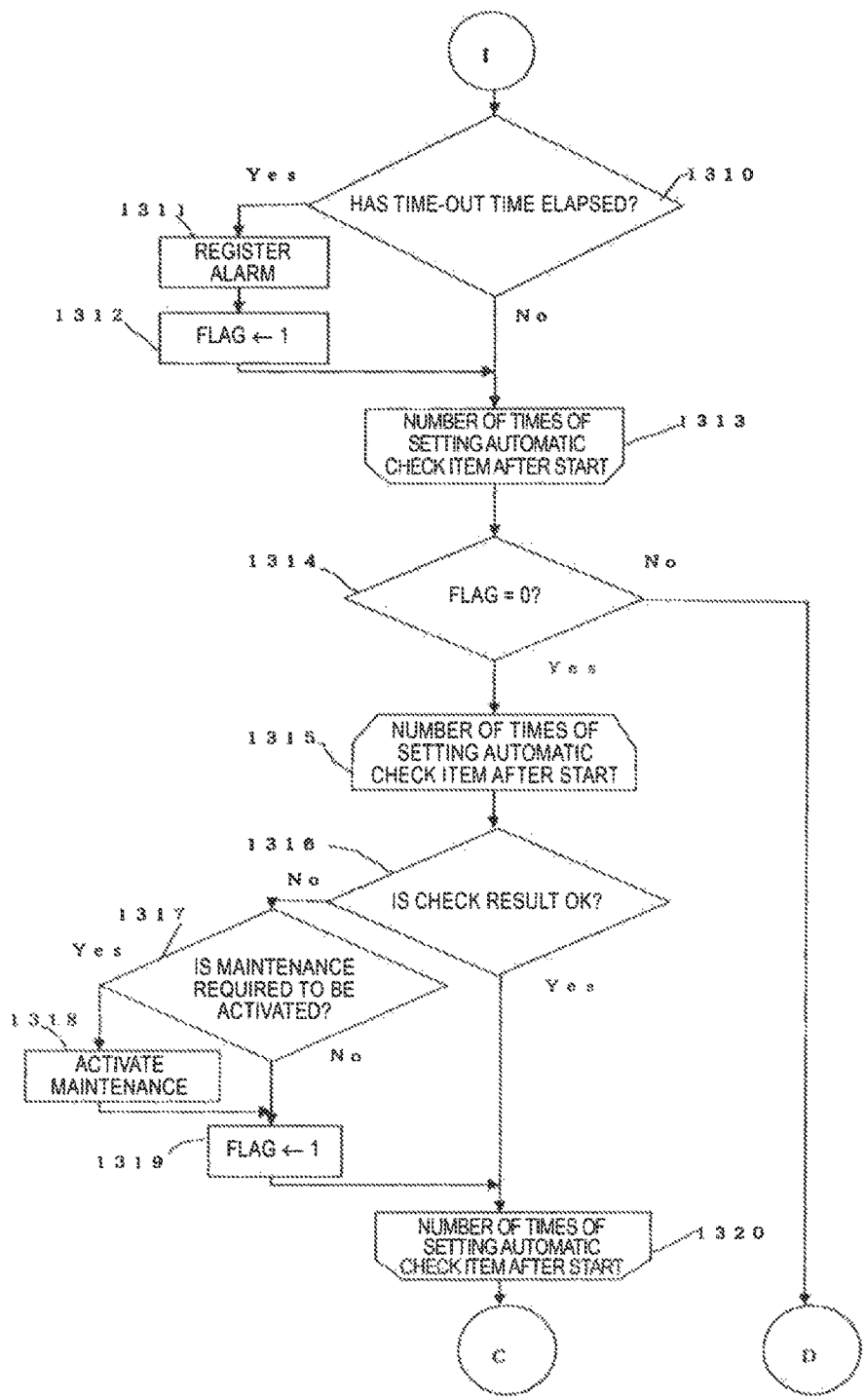

[Fig. 15]
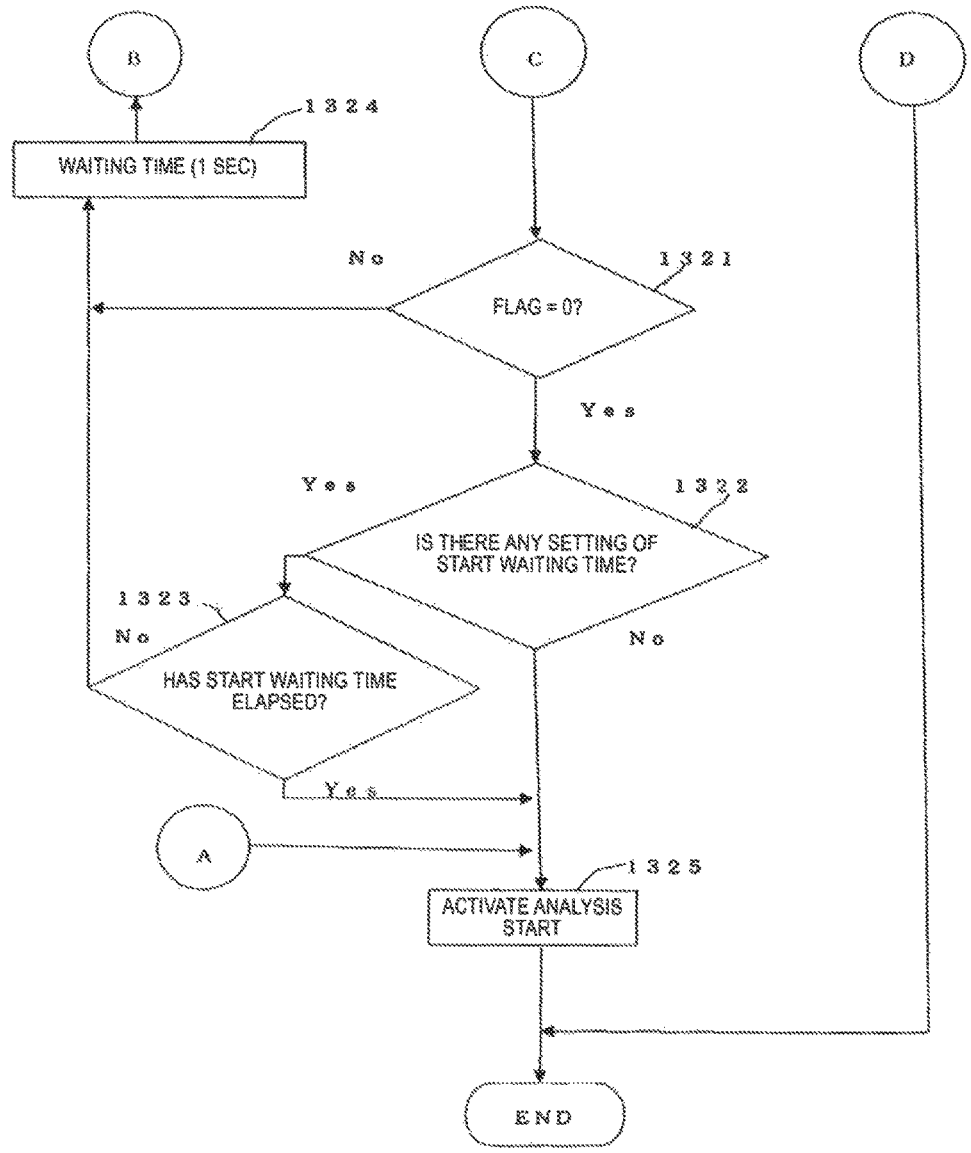

[Fig. 16]
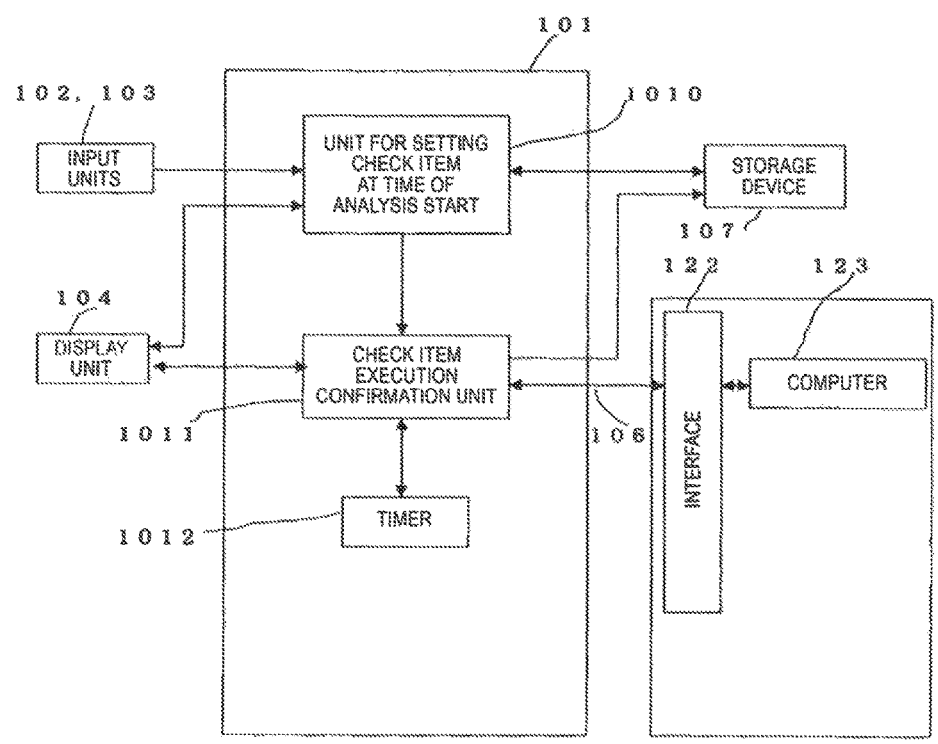

[Fig. 17]

[ EXAMPLE OF OUTPUT RESULT OF LOG INFORMATION ]

CHECK ITEM LOG INFORMATION AT TIME OF ANALYSIS START — 1401    14/01/14 11:01 — 1402

1. USER ID : OPERATOR 1    — 1403

2. ANALYSIS TIME : 14/01/10 20:51 – 14/01/11 05:39    — 1404

3. CHECK ITEM (PRESETTING)    — 1405
   - ■ CHECK REMAINING QUANTITY OF REAGENT
   - ■ CHECK WATER TEMPERATURE OF REACTION TANK
   - ■ [ EXCEEDING MAINTENANCE PERIOD ] REAGENT PRIMING (ANALYSIS MODULE 1)
   - ■ [ EXCEEDING MAINTENANCE PERIOD ] REACTION SYSTEM CLEANING (ANALYSIS MODULE 2)

4. CHECK ITEM (USER SETTING)    — 1406
   - ■ CONFIRM ARRIVAL OF HOST ORDER
   - ■ CONFIRM ACTIVATION OF PREPROCESSING SYSTEM
   - ■ CONFIRM POWER-ON OF PURE WATER DEVICE
   - ■ [ RECEIVED MESSAGE ] REAGENT BOTTLES (ALT, AST) HAVING REMAINING QUANTITY OF 0 REMAIN IN DEVICE
   - ■ [ RECEIVED MESSAGE ] TIP OF SAMPLE PROBE OF FIRST MODULE BECOMES CONTAMINATED.

6. NUMBER OF SAMPLE TO BE MEASURED    — 1407

| MODULE | GENERAL SAMPLE | GENERAL REEXAMINATION | EMERGENCY SAMPLE | EMERGENCY REEXAMINATION | STANDARD LIQUID | ACCURACY MANAGEMENT |
|---|---|---|---|---|---|---|
| ANALYSIS MODULE 1 | 100 | 10 | 20 | 2 | 12 | 4 |
| ANALYSIS MODULE 2 | 50 | 5 | 10 | 1 | 8 | 4 |
| ISE MODULE | 80 | 8 | 16 | 2 | 3 | 2 |
| TOTAL | 230 | 23 | 46 | 5 | 23 | 10 |

7. EXECUTION OF CLEANING MAINTENANCE : DONE    — 1408

[Fig. 18]
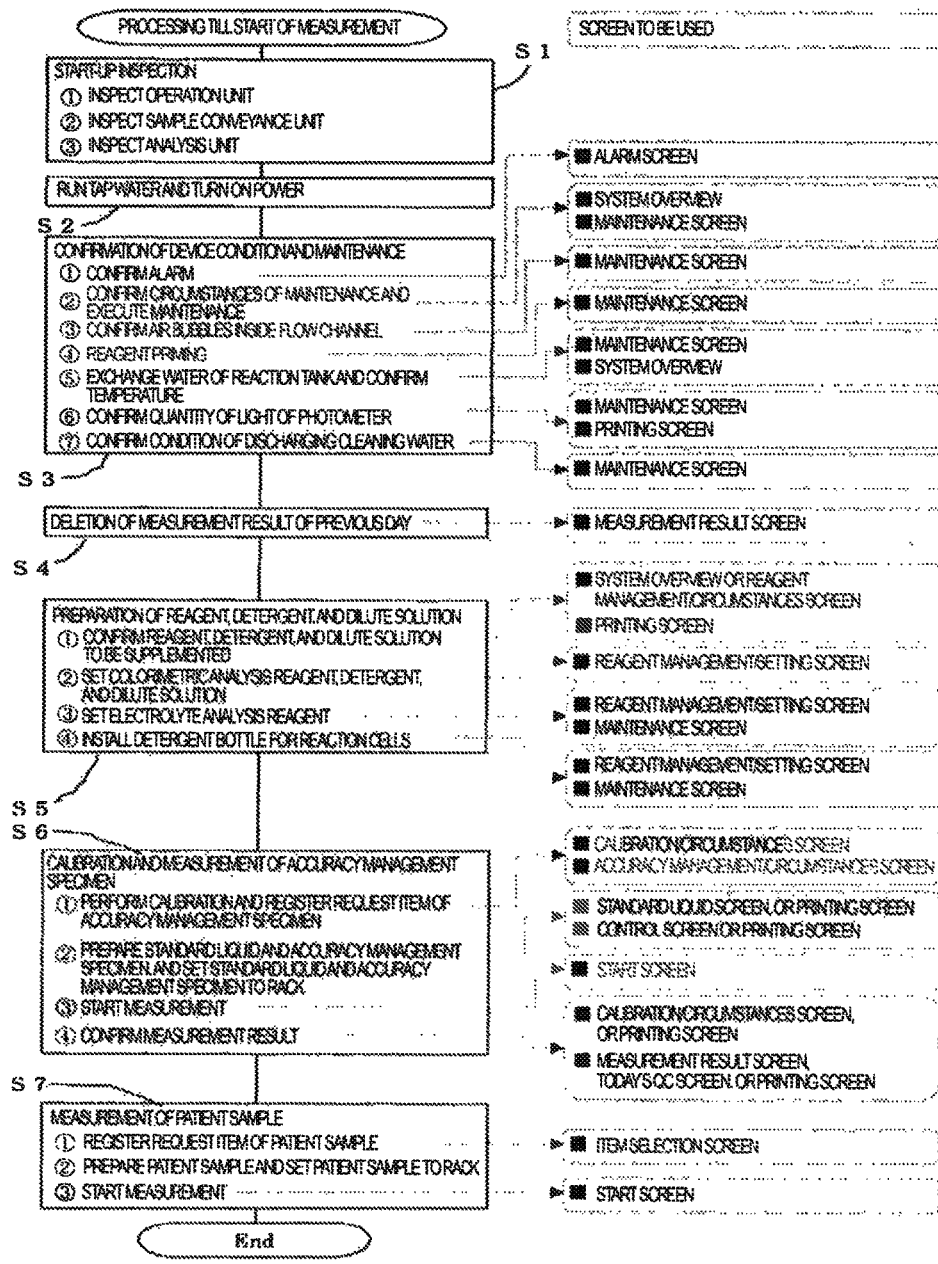

AUTOMATIC ANALYSIS DEVICE

TECHNICAL FIELD

The present invention relates to an automatic analysis device.

BACKGROUND ART

An automatic analysis device includes an analysis unit that has a mechanism system for measuring the concentration of a test substance in a sample, and an operation control unit. In the automatic analysis device, a test substance in a sample such as blood, urine, a body fluid, and the like is mixed with a reagent with respect to the test substance, inside a reaction container. A generated reactant is irradiated with light and the absorbance thereof is measured. Then, a quantitative analysis of the test substance is performed, and a measurement value is converted into concentration and a result thereof is output.

Before an analysis start, an operator sets the type of test sample, test items, and the like. Thereafter, a start-up inspection screen is displayed. As the start-up inspection, each unit of the device is visually inspected before power is turned on. Power is supplied to the automatic analysis device after opening a faucet of tap water and turning on power of a pure water device.

After the device starts to operate, the state of the device is confirmed based on the presence or absence of issuance of an alarm, and maintenance such as water exchange of a reaction tank, a photometer check, reagent priming, and the like is performed.

Thereafter, the water temperature of the reaction tank, the quantity of light of the photometer, and a relieved state of low-reagent inside a reagent flow channel are confirmed through the presence or absence of issuance of an alarm or visual recognition. A measurement result of a sample measured on the previous day is deleted, and a reagent, a detergent, and a dilute solution required for measuring the sample on the day are prepared and are set to the device, thereby starting an analysis of the sample.

At the timing of the analysis start, the device automatically performs a consistency check of an analysis method and analysis parameters such as prozone parameters, calibration parameters, and the like, thereby starting the analysis only when all of the analysis parameters are normally set. In a case where there is an error or inconsistency in the set analysis parameters, an alarm is issued and the analysis is stopped.

PTL 1 discloses an example of start-up inspection of an automatic analysis device.

CITATION LIST

Patent Literature

JP-A-09-196924

SUMMARY OF INVENTION

Technical Problem

A check which is automatically performed by a device at the time of an analysis start of a sample is mainly a consistency check for an analysis parameter. Other check items before the analysis start are required to be directly confirmed by an operator through the presence or absence of issuance of an alarm, or visual recognition.

Therefore, depending on a skill level of the operator related to handling the device, a difference is generated in the contents to be checked before the analysis start. For example, in a case where the operator is a person such as a night shift who is not skilled in handling the device, a check item before the analysis start is likely to be missed.

When a check item before the analysis start is missed, the possibility of measuring a sample becomes high while the state of the device is incomplete, thereby causing an erroneous report of a measurement result or a delay in report caused due to remeasurement.

An object of the present invention is to realize an automatic analysis device in which the check item at the time of the analysis start can be set in accordance with the skill level of an operator, the analysis can be performed after the check item is displayed and confirmed, and erroneous measurement caused due to a missed check can be prevented.

Solution to Problem

In order to achieve the above-described object, the present invention is configured as follows.

An automatic analysis device according to the present invention includes an analysis unit that measures a composition of a sample; and an operation control unit that includes an input device for giving an operational instruction of at least an analysis start to the analysis unit, a storage device storing each parameter of the operational instruction, and a display device displaying each parameter of the operational instruction and an analysis start screen.

The operation control unit stores a check item which is to be checked before an analysis operation, is input through the input device, and is required to be displayed in the analysis start screen, in the storage device; and causes the display device to display the check item which is to be checked before an analysis operation and is stored in the storage device, in the analysis start screen when an analysis start operation is performed.

Advantageous Effects of Invention

It is possible to realize an automatic analysis device in which the check item at the time of the analysis start can be set in accordance with the skill level of an operator, the analysis can be performed after the check item is displayed and confirmed, and erroneous measurement caused due to a missed check can be prevented.

BRIEF DESCRIPTION OF DRAWINGS

FIG. 1 is a schematic view in principle illustrating an overall configuration of an automatic analysis device in which an example of the present invention is applied.

FIG. 2 is a screen for setting a confirmation item required to be displayed, in accordance with the type of operator or the like, according to the example of the present invention.

FIG. 3 is a view illustrating a check item setting screen, according to the example of the present invention.

FIG. 4 is a day/time zone setting screen displayed through a display device of an operation control unit, according to the example of the present invention.

FIG. 5 is a maintenance period setting screen according to the example of the present invention.

FIG. 6 is a message list screen according to the example of the present invention.

FIG. 7 is a message input screen according to the example of the present invention.

FIG. 8 is an analysis start screen before execution of the check, according to the example of the present invention.

FIG. 9 is a view illustrating the analysis start screen after all of check items are checked, according to the example of the present invention.

FIG. 10 is a received message display screen according to the example of the present invention.

FIG. 11 is an alarm display screen according to the example of the present invention.

FIG. 12 is a flow chart of depicting processing of an analysis start button according to the example of the present invention.

FIG. 13 is a flow chart of analysis start activation determining processing.

FIG. 14 is the flow chart of the analysis start activation determining processing.

FIG. 15 is the flow chart of the analysis start activation determining processing.

FIG. 16 is a functional block diagram illustrating a function of setting the check item and a function of determining whether or not the displayed check item or the like is executed by an operator, included in the operation control unit, according to the example of the present invention.

FIG. 17 is a view illustrating an example of an output result of check item log information at the time of an analysis start.

FIG. 18 is a flow chart illustrating a flow of processing of inspection and the like performed before measurement starts.

DESCRIPTION OF EMBODIMENT

Hereinafter, an example of the present invention will be described with reference to the accompanying drawings.

EXAMPLE

FIG. 1 is a schematic view in principle illustrating an overall configuration of an automatic analysis device in which the example of the present invention is applied.

In FIG. 1, the reference sign 101 indicates an operation control unit. The operation control unit 101 is a computer including peripheral instruments such as a keyboard 102 for inputting data, a mouse 103, a display device 104 for displaying data, a printing device 105 for printing data, an interface 106 for being connected to an analysis unit, a storage device 107 for storing analysis instruction information and measurement results, and the like.

The reference sign 108 indicates the analysis unit, which is connected to the operation control unit 101 via the interface 106.

In the analysis unit 108, the reference sign 109 indicates a reaction disk, and multiple reaction containers 110 are installed on the concentric circumference thereof. The reference sign 111 indicates reagent bottles respectively containing various types of reagent, and a reagent suctioning tube 112 is connected to the bottle mouth thereof leading to a low-reagent sensor 125. On the periphery of the reaction disk 109, a sample dispensing mechanism 113, a stirring device 114, a cleaning device 115, a light source 116, and a multi-wavelength photometer 117 are individually disposed.

In the reaction disk 109, a reagent dispensing mechanism 118 is disposed and a reagent which has passed through the reagent suctioning tube 112 is supplied to the reagent dispensing mechanism 118. In addition, on the rotation circumference of the sample dispensing mechanism 113, a rack conveyance line 119 is installed. A rack 120 moves on the rack conveyance line 119. Multiple sample containers 121 respectively containing samples are laid in the rack 120.

All of operations of the mechanism of the above-described reaction disk 109 and the like are controlled by a computer 123 via an interface 122.

An operator gives an analysis instruction by using the display device 104, the keyboard 102, or the mouse 103 of the operation control unit 101. The analysis instruction is stored in the storage device 107 and is transmitted to the analysis unit 108 via the interface 106. In response to the received analysis instruction, the analysis unit 108 performs an analysis operation as follows.

The sample dispensing mechanism 113 dispenses a sample contained in the sample container 121 to the reaction container 110 as much as a predetermined quantity. When dispensing is completed with respect to one sample container 121, the rack 120 moves on the rack conveyance line 119 such that the next sample container 121 comes to a place immediately below the sample dispensing mechanism 113. When dispensing is completed with respect to all of the sample containers 121 on the rack 120, the rack 120 moves on the rack conveyance line 119 so as to be conveyed out.

The reaction container 110 having the dispensed sample rotatively moves on the reaction disk 109 due to a rotative operation of the reaction disk 109. In the meantime, the reagent dispensing mechanism 118 dispenses the reagent inside the reagent bottle 111 to the sample in the reaction container 110, the stirring device 114 stirs a reaction liquid, and measurement of absorbance is performed by the light source 116 and the multi-wavelength photometer 117. Thereafter, the reaction container 110 brought to an end of the analysis is cleaned by the cleaning device 115.

A measured absorbance signal is input to the computer 123 via an A/D converter 124 and the interface 122. In accordance with the absorbance signal, based on an analysis method which has been previously set for each test substance, in a case of a standard liquid sample, calibration curve data is calculated from set concentration data, and in cases of a patient sample and a control sample, the concentration data is calculated from the calibration curve data obtained through measurement of the standard liquid sample. As the measurement result, these pieces of data are subjected to addition of information in which the types of sample are symbolized. Thereafter, the data is transmitted to the operation control unit 101 via the interface 106.

The operation control unit 101 stores the received measurement result in the storage device 107 and outputs the measurement result to the display device 104 and the printing device 105.

Here, description will be given regarding a flow of processing of inspection and the like in the automatic analysis device performed before measurement starts.

FIG. 18 is a flow chart illustrating the flow of the processing of the inspection and the like performed before measurement starts.

In Step S1 of FIG. 18, the operator performs inspection of the operation control unit, a sample conveyance unit, and the analysis unit. In Step S2, the operator runs tap water and turns on power. Subsequently, in Step S3, the operator confirms the condition of the device and performs maintenance. In other words, the operator confirms an alarm, performs confirmation of circumstances and execution of maintenance, confirms air bubbles inside a flow channel, performs reagent priming, performs water exchange and temperature confirmation of a reaction tank, and confirms the condition of discharging cleaning water. In this Step S3, an alarm screen, a maintenance screen, and a printing screen displayed through the display device 104 are used.

In addition, in Step S4, the operator deletes the measurement result of the previous day by using a measurement result screen. Subsequently, in Step S5, the operator prepares the reagent, a detergent, and a dilute solution. In other words, the operator confirms the reagent, the detergent, and the dilute solution to be supplemented. The operator sets a colorimetric analysis reagent, the detergent, and the dilute solution. The operator sets an electrolyte analysis reagent and installs a detergent bottle for reaction cells. In this Step S5, a system overview or reagent management/circumstances screen, the printing screen, a reagent management/setting screen, and the maintenance screen are used.

Subsequently, Step S6 is an analysis start processing step, which is a step in which calibration is performed, an accuracy management specimen is measured, and the measurement result is confirmed. In other words, the operator performs the calibration, registers a request item of the accuracy management specimen, prepares a standard liquid and the accuracy management specimen, sets the standard liquid and the accuracy management specimen to the rack, and gives an instruction to start measurement. Then, the operator confirms the measurement result. In this case, measurement of the calibration and the accuracy management specimen is automatically performed by the automatic analysis device in accordance with set conditions. In addition, the operator gives an instruction of starting measurement by using a start screen.

In Step S7, the patient sample is measured. In other words, the operator registers the request item of the patient sample, prepares the patient sample, sets the patient sample to the rack, and gives an instruction to start measurement. In this case, the operator gives an instruction by using an item selection screen and the start screen.

In the example of the present invention, a confirmation item (check item which is to be checked before an analysis operation) required to be displayed in the start screen in which an instruction to start measurement is given at the time of the analysis start in Step S6 can be set for each type of operator. According to the configuration, when the set confirmation item is not checked, measurement is inhibited from starting, in principle.

FIG. 2 is a view illustrating a check item setting list screen displayed through the display device 104 of the operation control unit 101, according to the example of the present invention. FIG. 2 is a screen for setting the confirmation item required to be displayed, in accordance with the type of operator or the like.

In FIG. 2, a check name is displayed in the corresponding line of check item setting information No. 201 in a check item setting information list 202. The check name is a name of the check item setting information which is registered in a check item setting screen described below.

When an arbitrary line is selected in the list 202 and an edit button 203 is pressed, the check item setting screen (FIG. 3) is displayed. In FIG. 2, when the line displaying the check name in the list 202 is selected and a delete button 204 is pressed, the check item setting information of the selected check name is deleted. In a case where a line displaying no check name in the list 202 is selected, the delete button 204 is in an inactive display state and cannot be pressed.

FIG. 3 is the check item setting screen displayed through the display device 104 of the operation control unit 101, according to the example of the present invention. As described above, this screen is displayed by pressing the edit button 203 of FIG. 2. In a case where the line displaying the check name in the check item setting list 202 illustrated in FIG. 2 is selected and the edit button 203 is pressed, the check item setting information (FIG. 3) of the check name retained in the storage device 107 is displayed in the screen. In a case where a line displaying no check name in the list 202 of FIG. 2 is selected and the edit button 203 is pressed, a check item setting screen for new registration is displayed.

In the check item setting screen illustrated in FIG. 3, the operator sets a check name 301 as the check item setting information. In addition, a target user 302 is set. Here, in the target user 302, any one of designating a user level such as operator, supervisor, and administrator, and designating a user ID can be selected. In addition, when a day/time zone setting button 303 is pressed, a day/time zone setting screen described below is displayed. In addition, a maintenance period check 304 is set.

Here, when the operator checks the maintenance period check 304, if there is an item exceeding a maintenance period among maintenance items which are set so as to be required to be checked at the time of the analysis start in a maintenance period setting screen described below, the item is displayed in the analysis start screen described below, as a preset check item previously prepared in the device.

In addition, in the check item setting screen, the operator can set a selective check 305, the number 307 of consecutive times, and a time-out value 308 for each preset check item 306. Here, the preset check item 306 itself cannot be edited. In addition, when the selective check 305 is checked, the selective check 305 is displayed in the analysis start screen as the preset check item.

In addition, the number 307 of consecutive times is used in a case of a check item which is no longer necessary to be displayed in the screen at the time of the analysis start in the middle of the process because the check item is habituated as routine work such as supplement of the reagent before the analysis start. The check item of which the number of times of consecutive checks performed by the same operator at the time of the analysis start has reached the number 307 of consecutive times is not displayed in the analysis start screen thereafter, in a manner similar to a case where the selective check 305 is unchecked.

In addition, the time-out value 308 is used as the maximum time of a waiting time of the check item which automatically starts after waiting until the water temperature of the reaction tank, the quantity of light of a photometer, or the like reaches a value within a specification, after a analysis start button described below is pressed, and the maximum number of times of the repetitive number of times of a reagent priming operation when the reagent priming operation automatically starts after waiting until a low-reagent state of the reagent is relieved, similarly after the analysis start button is pressed.

In a case where the water temperature of the reaction tank, the quantity of light of the photometer, or the like does not come within the specification or the low-reagent state of the reagent is not relieved even after waiting till the time-out value 308 after the analysis start button is pressed, the alarm is configured to be displayed in an alarm display screen described below so as not to start an analysis.

In addition, in the check item setting screen, a check item 310 to be set by a user (operator), a selective check 309, and the number 311 of consecutive times are set. Here, the check item 310 to be set by the user can be freely edited by the operator. In addition, when the selective check 309 is checked, the selective check 309 is displayed in the below-described analysis start screen as a user setting check item.

In addition, the number 311 of consecutive times has a function similar to that of the number 307 of consecutive times.

In the check item setting screen, when the operator presses a registration button 313, set check information is retained in the storage device 107, and the screen is closed. In addition, in a case where a cancel button 312 is pressed, the screen is closed without retaining the set check information in the storage device 107.

FIG. 4 is the day/time zone setting screen displayed through the display device 104 of the operation control unit 101, according to the example of the present invention. The day/time zone setting screen is displayed when the day/time zone setting button 303 of FIG. 3 is pressed. In a case of the check item setting information which is already retained in the storage device 107, day/time zone setting information therein is displayed in the screen. In a case of new check item setting information, day/time zone setting information for new registration is displayed in the screen.

In the day/time zone setting screen illustrated in FIG. 4, the day and the time zone in which the check item setting information is displayed in the analysis start screen at the time of the analysis start is set. Here, the day is designated with a day selective check 401, and the time zone of each day is designated with a time zone designation pulldown list 402.

When a registration button 404 is pressed, the set check information is retained in the storage device 107, and the screen is closed. In a case where a cancel button 403 is pressed, the screen is closed without retaining the set check information in the storage device 107.

FIG. 5 is the maintenance period setting screen displayed through the display device 104 of the operation control unit 101, according to the example of the present invention. In FIG. 5, regarding the maintenance item selected from a maintenance item list 501 of the configuration unit of the automatic analysis device, in a case where maintenance period setting information is already retained in the storage device 107, the information is displayed in the screen. In a case where the maintenance period setting information is not retained in the storage device 107, a display for new registration is provided.

When setting the maintenance period illustrated in FIG. 5, for each maintenance item, a value 502 of the maintenance period, a unit 503 (time/date/month) of the maintenance period, the counting method (real time, power-on, operation) 504 of the maintenance period, and a check 505 at the time of the analysis start are set. The operation control unit 101 determines whether or not the maintenance item has exceeded the maintenance period at the time of the analysis start. Even though maintenance item has exceeded the maintenance period, when the maintenance is not executed, in a case of the check item setting information of which the maintenance period check 304 is checked in the check item setting screen described in FIG. 3, the name of the maintenance item is displayed in the analysis start screen as the preset check check item.

Moreover, in a case where the check 505 at the time of the analysis start of the maintenance item which has exceeded the maintenance period is checked, the analysis start cannot be carried out unless maintenance is executed.

When a registration button 507 illustrated in FIG. 5 is pressed, the set maintenance period setting information is retained in the storage device 107, and the screen is closed. In a case where a cancel button 506 is pressed, the screen is closed without retaining the set maintenance period setting information in the storage device 107.

FIG. 6 is the message list screen displayed through the display device 104 of the operation control unit 101, according to the example of the present invention. A beginning portion of a message registered through a message input screen described below is displayed in a line of a reference sign 601 which is the corresponding message No. in a message list 602. When an arbitrary line is selected from the list 602 and an edit button 603 is pressed, the message input screen is displayed.

When a line displaying a beginning portion of a message is selected from the list 602 and a delete button 604 is pressed, the selected input message is deleted. In a case where a line displaying no beginning portion of a message is selected from the list 602, the delete button 604 is in an inactive display state and cannot be pressed.

FIG. 7 is the message input screen displayed through the display device 104 of the operation control unit 101, according to the example of the present invention. This message input screen is displayed when the edit button 603 of FIG. 6 is pressed. In a case where a line displaying a beginning portion of a message is selected from the message list 602 and the edit button 603 is pressed, the input message information corresponding to the message No. 601 retained in the storage device 107 is displayed in the screen. In a case where a line displaying no beginning portion of a message is selected from the list 602 and the edit button 603 is pressed, the message input screen for new registration is displayed.

In the message input screen illustrated in FIG. 7, a message transmission target user 701, a message 702, and a check 703 at the time of the analysis start are set. Here, in the target user 701, any one of designating the user level such as operator, supervisor, and administrator, and designating the user ID can be selected. In addition, the message 702 can be freely edited by the operator in a text inputting-type method. In addition, the registered input message 702 can be confirmed in the analysis start screen by the operator corresponding to the transmission target user 701. Moreover, in a case where the check 703 at the time of the analysis start is checked, the analysis start cannot be carried out unless the operator confirms the message.

When a registration button 705 is pressed, the input message information is retained in the storage device 107 and the screen is closed. In addition, in a case where a cancel button 704 is pressed, the screen is closed without retaining the input message information in the storage device 107.

FIG. 8 is the analysis start screen before execution of the check the check item, displayed through the display device 104 of the operation control unit 101, according to the example of the present invention. Pieces of information in which the operator matches the set information of the set target user 302 and the date/time when the analysis start screen is opened match the set day/time zone 401 and 402 of FIG. 4 are respectively displayed in a preset check item list 802 and a user setting check item list 806 from the information set in the check item setting screen of FIG. 3.

In a case where there are multiple pieces of the check item setting information matching the operator and the date/time when the screen is opened, information having a lower check item setting information No. 201 takes precedence over others in the check item setting list screen of FIG. 2. Meanwhile, among the check items of the check item setting information, an item in which the number of times of consecutive checks at the time of the analysis start performed by the same operator reaches the number 307 of consecutive times in the check item setting screen is in a non-display state in the check item lists 802 and 806. In addition, in a case where the maintenance period check 304 is checked in the check item setting information, the maintenance item which has exceeded the maintenance period is also displayed in the preset check item list 802.

In addition, in a case where a message having the operator as a target is registered through the message input screen of FIG. 7, the beginning portion of the message is displayed in the user setting check item list 806.

Regarding the preset check item in the analysis start screen before execution of the check, illustrated in FIG. 8, in the preset check item set in the check item setting screen of FIG. 3 and the item of which the check 505 at the time of the analysis start in the maintenance period setting screen of FIG. 5 is checked among the items exceeding the maintenance period, a checkbox is displayed in the column of a confirmation check 801. In the checkbox, an item which the device does not automatically check among the check items set in the check item setting screen can be checked by the operator through a manual input, and an item other than that cannot be manually input.

In addition, in a case where an item which the device automatically checks among the check items set in the check item setting screen, or an item exceeding the maintenance period is selected on the lists 801 and 802, an execution button 803 can be pressed. In a case where the execution button 803 is pressed, the check or the maintenance is executed. In a case where the result of the check is OK, or the maintenance normally ends, the checkbox of the confirmation check 801 of the item is automatically checked.

In addition, in a case where an item which can be automatically checked after the analysis start button is pressed among the check items set in the check item setting screen, or an item exceeding the maintenance period is selected on the lists 801 and 802, an execution button 804 after start can be pressed. In a case where the execution button 804 is pressed, the checkbox of the confirmation check 801 of the item at that timing is automatically checked. The check or the maintenance is automatically executed after an analysis start button 808 is pressed.

Subsequently, regarding the user setting check item in the analysis start screen before execution of the check, in the user setting check item set in the check item setting screen of FIG. 3 and the item of which the check 703 at the time of the analysis start is checked in the message input screen of FIG. 7 among the messages having the operator as a target, a checkbox is displayed in the column of a confirmation check 805.

The checkbox of the user setting check item can be checked by the operator through a manual input, and the checkbox of the message cannot be manually input. In addition, in a case where the message is selected on the lists 805 and 806, a display button 807 can be pressed. In a case where the display button 807 is pressed, a received message display screen described below is displayed. After the received message display screen is closed, the message is presumed to be confirmed, and the checkbox of the confirmation check 805 of the message is automatically checked.

Meanwhile, a received message can be deleted in the received message display screen, when the received message is deleted and the displaying returns to the analysis start screen before execution of the check, in a case where the message is selected on the lists 805 and 806, the display button 807 cannot be pressed.

Until all of the checkboxes displayed in the confirmation checks 801 and 805 are checked by checking performed through the above-described automatic execution or a manual input, the analysis start button 808 is in an inactive display state as illustrated, and cannot be pressed. In other words, the operation control unit 101 determines whether or not checking is input by the operator for all of the checkboxes, and only when it is determined that checking is input for all of the checkboxes, the analysis operation is allowed to start.

However, an emergency start button 810 is prepared in case of circumstances where an analysis has to be immediately started due to an occurrence of an urgent sample, or the like. The emergency start button 810 can be pressed even if the confirmation checks 801 and 805 are not checked. In a case where the emergency start button 810 is pressed, regardless of the presence or absence of the automatic checking after the analysis start button is pressed, an analysis is immediately started and the screen is closed.

When a registration button 812 is pressed, the check information or start waiting time information 809 manually input through the confirmation checks 801 and 805 is retained in the storage device 107, and the screen is closed. In a case where a cancel button 811 is pressed, the screen is closed without retaining the check information or the start waiting time information 809 manually input through the confirmation checks 801 and 805 in the storage device 107. Meanwhile, in an item of which the confirmation checks 801 and 805 are automatically checked, the information thereof is retained in the storage device 107 at the timing when being checked. The start waiting time can be a time after an analysis start button 908 is pressed or can be a time from a point of time other than that.

FIG. 9 is a view illustrating the analysis start screen after checking all of the check items displayed through the display device 104 of the operation control unit 101, according to the example of the present invention. The reference signs 901 to 912 of FIG. 9 and the reference signs 801 to 812 of FIG. 8 indicate the same. When all of the check items are checked, the analysis start button 908 (corresponding to the analysis start button 808 of FIG. 8) is in an active display state and can be pressed. Accordingly, a normal analysis start can be carried out.

When the analysis start button 908 is pressed, an analysis, or automatic checking after the analysis start button is pressed starts, and the screen is closed. In addition, after the analysis start button 908 is pressed, at the timing when the analysis starts, the check information of the confirmation checks 901 and 905 is initialized.

FIG. 10 is the received message display screen displayed through the display device 104 of the operation control unit 101, according to the example of the present invention. The received message display screen is displayed when the received message display button 807 of FIG. 8 is pressed.

In the received message display screen, a received message 1001, a message sender's user ID 1002, and a message transmission date/time 1003 are displayed.

In addition, when a cancel button 1004 is pressed, the screen is closed without deleting the displayed information of the received message from the storage device 107. In a case where a delete button 1005 is pressed, the displayed information of the received message is deleted from the storage device 107, and the screen is closed.

FIG. 11 is the alarm display screen displayed through the display device 104 of the operation control unit 101, according to the example of the present invention. The alarm display screen is a screen for displaying contents as alarm information in a case where abnormality occurs while maintenance is executed with respect to a maintenance execution item after the analysis start button 908 is pressed or the automatic check item, the water temperature of the reaction tank, the quantity of light of the photometer, or the like does not reach the value within the specification even after waiting till the time-out value 308, or the low-reagent state of the reagent is not relieved.

In the alarm display screen, alarm codes 1101 and 1106, an alarm generation site 1102, alarm levels 1103 and 1107, an alarm name 1104, an alarm generation date/time 1105, description of an alarm 1108, and countermeasures for an alarm 1109 are displayed.

When a delete button 1110 is pressed in the alarm screen, the alarm information in the line selected from the alarm information lists 1101 to 1105 is deleted from the storage device 107. When a close button 1111 is pressed, the alarm display screen is closed.

FIG. 12 is a flow chart of depicting processing of the analysis start button in the analysis start screen executed by the operation control unit 101, according to the example of the present invention. The depicting processing is activated when the analysis start screen is opened and the display of the analysis start screen is updated.

In FIG. 12, first, "HAVE ALL OF PRESET CHECK ITEMS BEEN CHECKED?" is determined in Step 1201. In a case of No, "DEPICT ANALYSIS START BUTTON IN INACTIVE STATE" is executed in Step 1204.

In addition, when all of the preset check items have been checked in Step 1201, that is, in a case of Yes, "HAVE ALL OF USER SETTING CHECK ITEMS BEEN CHECKED?" is determined in Step 1202. In a case of No, "DEPICT ANALYSIS START BUTTON IN INACTIVE STATE" is executed in Step 1204. In Step 1202, when all of the user setting check items have been checked, that is, in a case of Yes, "DEPICT ANALYSIS START BUTTON IN ACTIVE STATE" is executed in Step 1203.

FIG. 13 to FIG. 15 are a flow chart of analysis start activation determining processing. The analysis start activation determining processing is activated when the analysis start button 908 or the emergency start buttons 810 and 910 are pressed.

In addition, FIG. 16 is a functional block diagram illustrating a function of setting the check item and a function of determining whether or not the displayed check item or the like is executed by the operator, among the functions which the operation control unit 101 has, according to the example of the present invention.

As illustrated in FIG. 16, the above-described check item at the time of the analysis start is designated by using the keyboard 102 or the mouse 103, the designated check item is set through a unit 1010 for setting the check item at the time of the analysis start, and the set check item is stored in the storage device 107. At the time of the analysis start, the set contents are read out from the storage device 107 by the unit 1010 for setting the check item at the time of the analysis start and is displayed through the display unit (the display device) 104. Instructions, data, and the like input by using the input units 102 and 103 are configured to be displayed through the display unit 104.

When checking process at the time of the analysis start starts, a check item execution confirmation unit 1011 reads out the contents of the set check item from the storage device 107, in accordance with the instruction from the unit 1010 for setting the check item at the time of the analysis start. The check item execution confirmation unit 1011 checks whether or not the operator has confirmed the check item, through the contents or the like displayed in the display unit 104. In addition, the check item execution confirmation unit 1011 activates a timer 1012, thereby counting the start waiting time or the like.

When it is determined that the operator has confirmed the check item, the check item execution confirmation unit 1011 delivers an analysis start command to the computer 123 via the interfaces 106 and 122.

The operational flow chart in FIGS. 13 to 15 mainly illustrates processing performed by the check item execution confirmation unit 1011.

Subsequently, the operational flow chart illustrated in FIGS. 13 to 15 will be described.

First, "PRESSED IS EMERGENCY START BUTTON?" of FIG. 13 is determined in Step 1301. In a case of Yes, the process proceeds to Step 1325 illustrated in FIG. 15 so as to end the processing of "ACTIVATE ANALYSIS START PROCESSING".

In Step 1301 of FIG. 13, in a case where "PRESSED IS EMERGENCY START BUTTON?" is No, "0 IS SET FOR FLAG" (Step 1302), and "IS MAINTENANCE CURRENTLY EXECUTED FOR AUTOMATIC CHECK ITEM?" is determined (Step 1304) as many times as "NUMBER OF TIMES OF SETTING AUTOMATIC CHECK ITEM AFTER ANALYSIS START BUTTON IS PRESSED" (Steps 1303 and 1306). Only in a case of Yes, "1 IS SET FOR FLAG" (Step 1305) is executed.

After ending the determination of the processing of Steps 1304 and 1305 performed as many times as "NUMBER OF TIMES OF SETTING AUTOMATIC CHECK ITEM AFTER ANALYSIS START BUTTON IS PRESSED" (Steps 1303 and 1306), "IS FLAG 0?" is determined (Step 1307). In a case of No, after "WAITING TIME OF 1 SECOND" (Step 1308), the process restarts from the processing Step 1302.

In Step 1307, in a case where "IS FLAG 0?" is Yes, "HAS TIME-OUT TIME SET IN CHECK ITEM SETTING SCREEN REGARDING AUTOMATIC CHECK ITEM ELAPSED?" is determined (Step 1310) as many times as "the number of times of setting the automatic check item after the analysis start button is pressed" (Steps 1309 and 1313). Only in a case of Yes, "ALARM IS REGISTERED" (Step 1311), and "1 IS SET FOR FLAG" (Step 1312) is executed.

After ending the determination of the processing of Steps 1310 to 1312 performed as many times as "NUMBER OF TIMES OF SETTING AUTOMATIC CHECK ITEM AFTER ANALYSIS START BUTTON IS PRESSED" (Step 1309 and 1313), "IS FLAG 0?" is determined (Step 1314). In a case of No, the processing ends.

In Step 1314, in a case where "IS FLAG 0?" is Yes, "IS CHECK RESULT OF AUTOMATIC CHECK ITEM OK?" (Step 1316) is determined as many times as "NUMBER OF TIMES OF SETTING AUTOMATIC CHECK ITEM AFTER ANALYSIS START BUTTON IS PRESSED" (Step 1315 and 1320). Only in a case of No, "IS MAINTENANCE OF AUTOMATIC CHECK ITEM REQUIRED TO BE ACTIVATED?" (Step 1317) is determined. In a case of Yes, "MAINTENANCE OF AUTOMATIC CHECK ITEM IS ACTIVATED" (Step 1318), and "1 IS SET FOR FLAG" (Step 1319). In Step 1317, in a case where "IS MAINTENANCE REQUIRED TO BE ACTIVATED?" is No, "1 IS SET FOR FLAG" (Step 1319).

After ending the determination of the processing of Steps 1317 to 1319 performed as many times as "NUMBER OF TIMES OF SETTING AUTOMATIC CHECK ITEM AFTER ANALYSIS START BUTTON IS PRESSED" (Step 1315 and 1320), "IS FLAG 0?" is determined (Step 1321). In a case of No, after "WAITING TIME OF 1 SECOND" (Step 1324), the process restarts from the processing Step 1302.

In Step 1321, in a case where "IS FLAG 0?" is Yes, "IS THERE ANY SETTING FOR START WAITING TIME OF ANALYSIS START SCREEN?" is determined (Step 1322). In a case of No, "ANALYSIS START PROCESSING IS ACTIVATED" (Step 1325), and the processing ends.

In Step 1322, in a case where "IS THERE ANY SETTING OF START WAITING TIME?" is Yes, "HAS START WAITING TIME ELAPSED?" is determined (Step 1323). In a case of No in Step 1323, after "WAITING TIME OF 1 SECOND" (Step 1324), the process restarts from the processing 1302.

In Step 1323, in a case of Yes, "ANALYSIS START PROCESSING IS ACTIVATED" (Step 1325), and the processing ends.

FIG. 17 is a view illustrating an example of an output result of check item log information at the time of the analysis start. The log information illustrated in FIG. 17 is retained in the storage device 107 by the operation control unit 101 for each term from the analysis start to the analysis end. The log information is output to an external media such as the display device 104, the printing device 105, a USB, and the like based on the output instruction input through the input devices 102 and 103.

The output information is a title 1401 of the log information, an output date/time 1402 of the log information, a user ID 1403 of the operator who performed the analysis operation, a start time/end time of analysis 1404, a preset check item 1405 checked at the time of the analysis start, a user setting check item 1406 checked at the time of the analysis start, information 1407 of the number of measurement samples for the sample type and the analysis module, and the presence or absence 1408 of execution of cleaning maintenance at the time of the analysis end.

As described above, according to the present invention, the check item such as checking the remaining quantity of a reagent or the like displayed in the check screen before the analysis start can be set for each type of operator, each day, each time. The set check item is configured to be displayed in the screen before the analysis start, and unless the operator confirms the check item, the analysis start is not allowed in principle.

Therefore, it is possible to realize an automatic analysis device which can prevent erroneous measurement caused due to a missed check of the operator before the analysis start, and it is possible to prevent an erroneous report of the measurement result caused due to a missed check, and a delay in report caused due to remeasurement.

REFERENCE SIGNS LIST

101 . . . OPERATION CONTROL UNIT, 102 . . . KEYBOARD, 103 . . . MOUSE, 104 . . . DISPLAY DEVICE, 105 . . . PRINTING DEVICE, 106 . . . INTERFACE, 107 . . . STORAGE DEVICE, 108 . . . ANALYSIS UNIT, 109 . . . REACTION DISK, 110 . . . REACTION CONTAINER, 111 . . . REAGENT BOTTLE, 112 . . . REAGENT SUCTIONING TUBE, 113 . . . SAMPLE DISPENSING MECHANISM, 114 . . . STIRRING DEVICE, 115 . . . CLEANING DEVICE, 116 . . . LIGHT SOURCE, 117 . . . MULTI-WAVELENGTH PHOTOMETER, 118 . . . REAGENT DISPENSING MECHANISM, 119 . . . RACK CONVEYANCE LINE, 120 . . . RACK, 121 . . . SAMPLE CONTAINER, 122 . . . INTERFACE, 123 . . . COMPUTER, 124 . . . A/D CONVERTER, 125 . . . LOW-REAGENT SENSOR, 202 . . . CHECK ITEM SETTING INFORMATION LIST, 301 . . . AREA FOR INPUTTING NAME OF CHECK ITEM TO BE SET, 302 . . . AREA FOR SETTING TARGET USER OF CHECK ITEM TO BE SET, 303 . . . TARGET DAY/TIME ZONE SETTING SCREEN DISPLAY BUTTON FOR CHECK ITEM TO BE SET, 304 . . . CHECKBOX FOR DETERMINING WHETHER OR NOT TO CHECK MAINTENANCE PERIOD, 306 . . . AREA FOR DISPLAYING NAME OF PRESET CHECK ITEM, 307 . . . AREA FOR INPUTTING NUMBER OF TIMES OF CONSECUTIVE CHECKS, 308 . . . AREA FOR INPUTTING TIME-OUT VALUE, 310 . . . AREA FOR INPUTTING USER SETTING CHECK ITEM, 311 . . . AREA FOR INPUTTING THRESHOLD OF NUMBER OF TIMES OF CONSECUTIVE CHECKS, 401 . . . CHECKBOX FOR SELECTING DAY, 402 . . . TIME DESIGNATION PULLDOWN LIST, 501 . . . MAINTENANCE ITEM LIST, 502 . . . AREA FOR INPUTTING VALUE OF MAINTENANCE PERIOD, 503 . . . MAINTENANCE PERIOD UNIT DESIGNATION PULLDOWN LIST, 504 . . . MAINTENANCE PERIOD COUNTING METHOD DESIGNATION PULLDOWN LIST, 602 . . . MESSAGE LIST, 701 . . . AREA FOR SETTING MESSAGE TRANSMISSION TARGET USER, 702 . . . AREA FOR INPUTTING MESSAGE, 801 . . . CHECKBOX, 802 . . . NAME OF PRESET CHECK ITEM, 806 . . . NAME OF USER SETTING CHECK ITEM, 808 . . . ANALYSIS START BUTTON (INACTIVE), 809 . . . AREA FOR INPUTTING START WAITING TIME, 810 . . . EMERGENCY ANALYSIS START BUTTON, 902 . . . NAME OF PRESET CHECK ITEM, 906 . . . NAME OF USER SETTING CHECK ITEM, 908 . . . ANALYSIS START BUTTON (ACTIVE), 1001 . . . AREA FOR DISPLAYING RECEIVED MESSAGE, 1010 . . . UNIT FOR SETTING CHECK ITEM AT TIME OF ANALYSIS START, 1011 . . . CHECK ITEM EXECUTION CONFIRMATION UNIT, 1012 . . . TIMER, 1101 . . . ALARM CODE, 1102 . . . ALARM GENERATION SITE, 1103 . . . ALARM LEVEL, 1104 . . . ALARM NAME, 1105 . . . ALARM GENERATION DATE/TIME, 1106 . . . ALARM CODE, 1107 . . . ALARM LEVEL, 1108 . . . DESCRIPTION OF ALARM, 1109 . . . COUNTERMEASURES FOR ALARM

The invention claimed is:
1. An automatic analysis device comprising:
an analysis unit configured to automatically perform a plurality of operations and to measure a composition of a sample; and
an operation control unit that includes an input device, a storage device configured to store a plurality of preset check items which are associated with the operations of the analysis unit, and a display device,
wherein the operation control unit is configured to display an analysis start screen through which the input device inputs an analysis start instruction,
wherein the operation control unit is further configured to:
store, before displaying the analysis start screen, at least one user check item, in the storage device;
display the analysis start screen which includes the preset check items, the user check item, a plurality of checkboxes corresponding to the preset check items and the user check item, an execute button, and an execute after start button;
receive, via the input device, a selection of one or more of the preset check items and a selection of the execute button which causes the analysis unit to automatically perform the one or more operations associated with the selected preset check items and, after the one or more operations are performed, cause checks to be automati- cally input in the checkboxes corresponding to the selected preset check items and displayed on the analysis start screen, receive, via the input device, a selection of another one or more of the preset check items and a selection of the execute after start button which causes the one or more operations associated with the other selected preset check items to be scheduled to be automatically performed once the analysis start instruction is input and, after the one or more operations associated with the other selected preset check items are scheduled, causes checks to be automatically input in the checkboxes corresponding to the other selected preset check items and displayed on the analysis start screen, receive, via the input device, manual input of checks in the checkboxes corresponding to the at least one user check item and causing the manually input checks to be displayed on the analysis start screen, only when the checks are displayed for all of the checkboxes on the analysis start screen, cause an analysis start button to appear in the analysis start screen;

receive, via the input device, a selection of the analysis start button;

when the selection of the analysis start button is received, instruct the analysis unit to automatically perform the scheduled one or more operations associated with the other selected preset check items; and when the scheduled one or more operations have been completed, instruct the analysis unit to start to measure the composition of the sample.

2. The automatic analysis device according to claim 1, wherein the at least one user check item is stored in the storage device for one or more predetermined types of operators, and the analysis start screen is displayed to include the at least one user check item according to a current type of operator.

3. The automatic analysis device according to claim 1, wherein the preset check items are stored in the storage device for one or more predetermined time periods, and the analysis start screen is displayed to include the preset check items according to a current time.

4. The automatic analysis device according to claim 1, wherein the preset check items are stored in the storage device in correspondence with predetermined maintenance periods, and the analysis start screen is displayed with the preset check items having corresponding maintenance periods which are exceeded by a current time.

5. The automatic analysis device according to claim 4, wherein the operation control unit is further configured to display, when the selection of the analysis start button has been received and when the scheduled one or more operations have not been completed, a notification that an abnormality occurs in the analysis unit.

6. The automatic analysis device according to claim 1, wherein the at least one user check item stored in the storage device corresponds to a message such as a report, an operating procedure, and the like for one or more specified operators and the analysis start screen is displayed with the user check item corresponding to the message and a display button, wherein the operation control unit is further configured to receive, via the input device, a selection of the user check item corresponding to the message and a selection of the display button which causes the analysis start screen to display the message, and wherein the manual input of a check in the checkbox of the user check item corresponding to the message is only able to be received after the message is displayed.

7. The automatic analysis device according to claim 1, wherein the analysis start screen is displayed to with an emergency start button, and wherein the operation control unit is further configured to receive, via the input device, a selection of the emergency start button which causes the analysis operation to start without the checks being displayed for all of the checkboxes on the analysis start screen.

8. The automatic analysis device according to claim 1, wherein preset check items are stored in the storage device in correspondence with predetermined thresholds for consecutive times of performance, and the analysis start screen is displayed to include the preset check items which have not reached the corresponding thresholds stored in the storage device.

9. The automatic analysis device according to claim 1, wherein the operation control unit is further configured to:
store, in the storage device, and display, on the display device, a user ID of an operator, an analysis start/end time or the like, and a number of samples or the like to be measured in the analysis operation.

10. The automatic analysis device according to claim 1, wherein the preset check items include to check a water temperature of a reaction tank, and a time-out time until the water temperature of the reaction tank comes within a predetermined specification, and the operation control unit is further configured to:
instruct the analysis unit to determine whether the water temperature of the reaction tank comes within the predetermined specification, and when the water temperature of the reaction tank does not come within the predetermined specification in a predetermined time period, output an alarm to the display device without instructing the analysis unit to start to measure the composition of the sample.

11. The automatic analysis device according to claim 1, wherein the preset check items include to check a quantity of light of a photometer, and a time-out time until the quantity of light of the photometer is settled within a predetermined specification, and the operation control unit is further configured to:
instruct the analysis unit to determine whether the quantity of light of the photometer is settled within the predetermined specification, and when the quantity of light of the photometer does not come within the predetermined specification in a predetermined time period, output an alarm to the display device without instructing the analysis unit to start to measure the composition of the sample.

12. The automatic analysis device according to claim 1, wherein the preset check items include to check a low-reagent state inside a reagent flow channel, and a number of permissible executions of reagent priming until the low-reagent state is relieved, and the operation control unit is further configured to:
instruct the analysis unit to determine whether the low-reagent state is relieved within the number of permissible executions of reagent priming, and when the low-reagent state is not relieved within the number of permissible executions of reagent priming, output an alarm to the display device without instructing the analysis unit to start to measure the composition of the sample.

13. The automatic analysis device according to claim 1, wherein the operation control unit is further configured to:
  receive, via the input device, a waiting time till the analysis start, and
  when the scheduled one or more operations have been completed, instruct the analysis unit to start after the waiting time has elapsed.

* * * * *